United States Patent
Fassina et al.

[11] Patent Number: 5,880,259
[45] Date of Patent: Mar. 9, 1999

[54] PEPTIDE USEFUL AS A LIGAND

[75] Inventors: Giorgio Fassina, Milan; Antonio Verdoliva, Castellammare Di Stabia; Menotti Ruvo, Trevico, all of Italy

[73] Assignee: Tecnogen S.C.p.A., Piana Di Monte Verna, Italy

[21] Appl. No.: 670,207

[22] Filed: Jun. 20, 1996

[30] Foreign Application Priority Data

Jun. 21, 1995 [IT] Italy .................................. MI95A1328
Apr. 29, 1996 [IT] Italy .................................. MI96A0831

[51] Int. Cl.⁶ ...................................................... C07K 7/02
[52] U.S. Cl. .......................... 530/326; 435/7.1; 435/226; 435/212; 435/215
[58] Field of Search .............................. 530/326; 435/7.1, 435/226, 212, 215

[56] References Cited

U.S. PATENT DOCUMENTS

| 5,141,862 | 8/1992 | Patel et al. | 435/226 |
| 5,227,297 | 7/1993 | Patel | 435/174 |
| 5,229,490 | 7/1993 | Tam . | |
| 5,286,654 | 2/1994 | Cox et al. | 436/501 |

FOREIGN PATENT DOCUMENTS

| A 0481930 | 4/1992 | European Pat. Off. . | |
| 188283 | 7/1995 | Japan . | |
| WO A 9218528 | 10/1992 | WIPO . | |

OTHER PUBLICATIONS

Fassina et al, Immunomethods, vol. 5, pp. 114–120, (1984).

*Primary Examiner*—Ponnathapura Achutamurthy
*Assistant Examiner*—T. D. Wesendorf
*Attorney, Agent, or Firm*—Nixon & Vanderhye, P.C.

[57] ABSTRACT

A peptide of formula (I)

$$(H_2N-X_1-Thr-X_2-CO)_n-R \qquad (I)$$

where $X_1$ and $X_2$, different one another, are an amino acid residue of arginine or tyrosine in configuration L or D, wherein the hydroxy group of threonine and tyrosine and the guanidine moiety of arginine may be protected by a compound conventionally used in peptide chemistry for protecting the hydroxy group and the guanidine moiety, respectively, n is 1, 2, 3 or 4, and R, when n is 2, 3 or 4, is a group suitable for forming a dimer, trimer or tetramer, while, when n is 1, R is OH, a single amino acid residue, or a peptide chain containing up to 7 amino acid residues.

1 Claim, 2 Drawing Sheets

AFFINITY CHROMATOGRAPHY
RABBIT IMMUNOGLOBULINS SEPARATION
WITH THE PEPTIDE OF EXAMPLES 1 AND 4

Fig. 2

ELECTROPHORETIC ANALYSIS OF RABBIT IMMUNOGLOBULINS PURIFIED BY AFFINITY CHROMATOGRAPHY WITH THE PEPTIDE OF EXAMPLES 1 AND 4

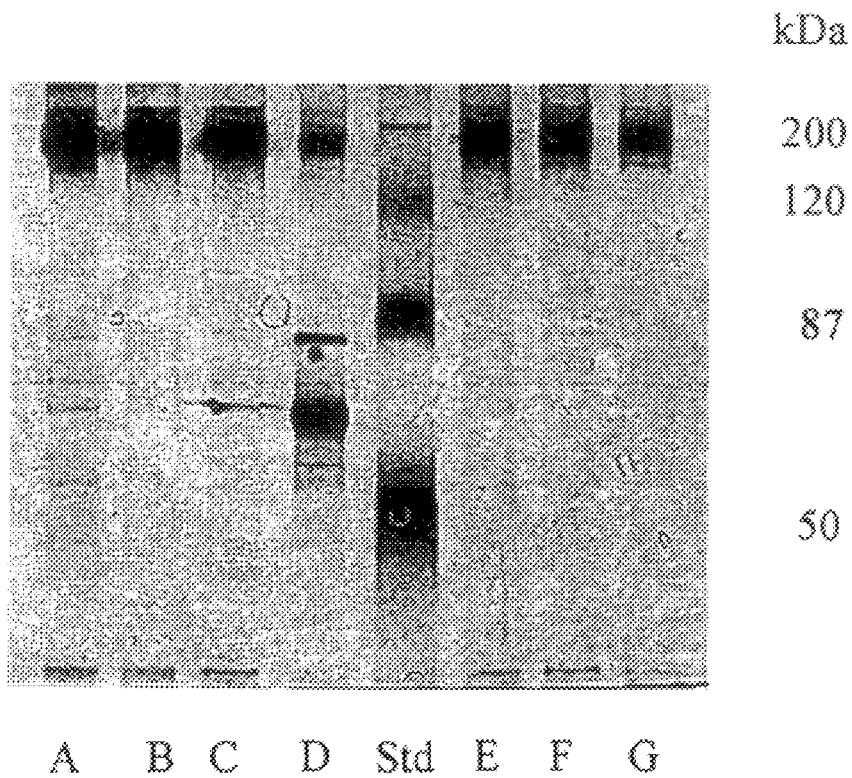

A: Bound material deriving from sample loading in 0.1 M ammonium acetate

B: Bound material deriving from sample loading in 0.1 M sodium phosphate pH 7.0

C: Bound material deriving from sample loading in 0.1 M sodium phosphate pH 8.5

D: Molecular weight standard

E: Bound material deriving from sample loading in 25 mM Bis-Tris pH 6.5

F: Bound material deriving from sample loading in 25 mM Bis-Tris pH 6.5

G: Bound material deriving from sample loading in 25 mM Bis-Tris pH 6.5

PEPTIDE USEFUL AS A LIGAND

This invention relates to a peptide useful as a ligand, the process for preparing thereof, and the use thereof as a immunoglobulins ligand.

More particularly, the present invention relates to a peptide capable of binding non covalently itself to the constant portion of immunoglobulins.

Immunoglobulins, also known as antibodies, are extremely important in diagnostic and therapeutic field. Indeed, in the first case they are widely used as reagents useful for the identification and quantification of compounds in biological fluids, while in the second case they are used as agents capable of binding themselves to biological molecules involved in physiological processes of therapeutic significance. In view of the above mentioned significance, their production, and above all their purification, are extremely important from an industrial point of view.

Immunoglobulins can be obtained from animal sera, or from cultivation of suitable cell lines.

Their purification is carried by means of conventional chromatographic techniques, such as ionic exchange or gel filtration, or preferably by affinity chromatography using columns prepared by immobilization of protein A, obtained from *Staphylococcus aureus*, which is capable of binding specifically itself to the constant portion of immunoglobulins [Siodahl, J. Eur. J., Biochem 78: 471–490 (1977)]. However, protein A suffers from many limitations when used on a large scale since its extractive origin calls for a careful control and a careful purification in order to avoid contamination of the product purified using said protein. In addition, protein A is not very stable to denaturing conditions and in the presence of agents used to remove biological contaminants such as viruses or nucleic acid fragments. Finally, the production cost of protein A is extremely high and limits its use in purifications on a large scale.

Therefore, there is still a great need for a synthetic ligand capable of mimicking protein A as far as the ability to recognize the constant portion of immunoglobulins is concerned, which however can be manufactured at low cost. Moreover, thanks to the synthetic origin, it would be devoid of biological contaminants.

It has now been found that these properties are shown by a peptide comprising the amino acid residues of arginine, threonine and tyrosine.

In particular, it has been found that the above mentioned properties are shown by a peptide comprising the sequence:

—HN—$X_1$—Thr—$X_2$—CO—  (S)

where
$X_1$ is an amino acid residue of arginine or tyrosine having configuration L or D,
$X_2$ is an amino acid residue of tyrosine or arginine having configuration L or D,

SUMMARY OF THE INVENTION

Thr is an amino acid residue of threonine having configuration L or D, provided, however, that $X_1$ is arginine when $X_2$ is tyrosine, and $X_1$ is tyrosine when $X_2$ is arginine.

Preferably, at least one amino acid residue of the sequence (S) has D configuration.

Even more preferably, two or all the three amino acid residues of the sequence (S) have D configuration.

It is therefore a first object of this invention to provide a peptide of formula (I)

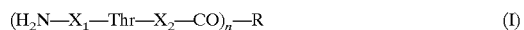
($H_2N$—$X_1$—Thr—$X_2$—CO)$_n$—R  (I)

where
$X_1$ and $X_2$, different one another, are an amino acid residue of arginine or tyrosine in configuration L or D, wherein the hydroxy group of threonine and tyrosine and the guanidine moiety of arginine may be protected by a compound conventionally used in peptide chemistry for protecting the hydroxy group and the guanidine moiety, respectively,
n is 1, 2, 3 or 4, and
R, when n is 2, 3 or 4, is a group suitable for forming a dimer, trimer or tetramer, while, when n is 1, R is OH, a single amino acid residue, or a peptide chain comprising up to 7 amino acid residues.

As used herein the terms "dimer", "trimer" and "tetramer" are intended to mean a peptide comprising 2, 3, or 4 sequences (S).

A typical example of a group suitable for forming a dimer (n=2) is a lysine residue. A typical example of a group suitable for forming a trimer (n=3) is a dipeptide lysil-lysine of formula Lys-Lys. A typical example of a group suitable for forming a tetramer (n=4) is a branched tripeptide of formula Lys-Lys($\epsilon$-Lys).

A typical example of a tetramer of formula (I) has the following formula

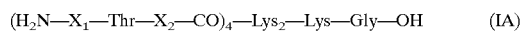
($H_2N$—$X_1$—Thr—$X_2$—CO)$_4$—Lys$_2$—Lys—Gly—OH  (IA)

where
$X_1$ and $X_2$ have the above mentioned meanings and wherein the hydroxy group of threonine and tyrosine and the guanidine moiety of arginine may be protected by a compound conventionally used in peptide chemistry for protecting the hydroxy group and the guanidine moiety, respectively.

Many protecting groups for protecting the hydroxy group in peptide synthesis are reported in the literature (G. A. Grant, Synthetic peptides: a user's guide, Freeman, N.Y., 1992).

Typical examples of said protecting groups are: ter-butyl (tBu) (La Joie, G. Crivici, A., Adamson, J. G. "Synthesis" 571–572 (1990)) and the benzyl group (Yojima "Tetrahedron" 44:805–819 (1988)).

Many groups useful for protecting the guanidine moiety of arginine are also known from the literature (Grant, G. A. Synthetic peptides: A user's guide, Freeman, N.Y., 1992).

Typical examples of said protecting groups are: 2,2,5,7, 8-pentamethylcroman-6-sulphonyl (Pmc) and 4-methoxy-2, 3,6-trimethylbenzene (Mtr) (Ramage & Green, "Tetrahedron Letters", 28,2287 (1987); Fujino et al. "Chem. Pharm. Bull.", 29,2825 (1981).

Typical examples of thus protected compounds of formula (I) are the compounds Boc—D—Arg(Pbf—D—Thr(tBu)—D—Tyr(tBu)—OMe of Example 1(d), and ($H_2N$—Arg (Pmc)—Thr(OtBu)—Tyr(OtBu)—CO)$_4$—Lys$_2$—Lys—Gly—OH of Example 2.

When n is 1 and R is a peptide comprising from one to seven amino acid residues, all the amino acids comprised in the sequence may be different or equal to each other and have L or D configuration. The D configuration is the preferred one. Furthermore, simple and cheap amino acids will be preferred.

Specific examples of R for n equal to 1 are, Gly or Ala, Gly-Gly, Gly-Ala, Ala-Gly, Ala-Ala, Gly-Gly-Gly, Ala-Ala- Ala, Gly-Gly-Gly-Gly (SEQ ID NO:1), Gly-Gly-Gly-Gly-Gly (SEQ ID NO:2), Gly-Ala-Gly-Ala-Gly (SEQ ID NO:3), Ala-Gly-Ala-Gly-Ala-Gly-Ala (SEQ ID NO:4).

The peptides of formula (I) may be readily prepared according to both the conventional liquid phase peptide preparation and solid-phase peptide preparation techniques.

The preparation according to the solid-phase technique is preferably carried out by means of an automatic synthesizer. A typical example of a suitable automatic synthesizer is the model 431 A from Applied Biosystems (Foster City, Calif., USA). Preferably, the preparation is performed according to the synthesis procedures recommended by the manufacturer, said procedures being usually based on known methods well described in the literature (Atherton & Sheppard, 1989, Solid Phase Peptide Synthesis: A practical approach, IRL Press, Oxford).

It is a third object of this invention to provide the use of a compound of formula (I) to form complexes with at least one immunoglobulin in a separation process of said immunoglobulin or mixture of immunoglobulins.

Examples of immunoglobulins capable of forming complexes owing to non covalent binding to compounds of formula (I), are: mouse IgG, rat IgG, chicken IgY, goat IgG, bovine IgG, human IgG, human IgA, and of other species, human IgM and of other species.

A typical example of a method for the separation and purification of an immunoglobulin comprises:

(i) immobilizing on an affinity chromatography support a compound capable of binding non covalently itself to at least one immunoglobulin, (ii) packing said affinity chromatography support in a chromatographic column, (iii) equilibrating said column with a buffer capable of promoting an interaction between immunoglobulin and the immobilized compound, (iv) loading said column with a fluid comprising at least one immunoglobulin, (v) washing said column with at least one liquid capable of eluting the impurities without interfering with the interaction between immunoglobulin and the immobilized compound, (vi) eluting said immunoglobulin previously adsorbed on the column with a dissociating eluent, and is characterized in that:

the compound capable of binding itself non covalently to at least one immunoglobulin is a compound of formula (I), where $X_1$, $X_2$, n and R have the meanings shown above.

Steps from (i) to (vi) are carried out according to conventional techniques.

Preferably, the support for affinity chromatography is preactivated with epoxide groups for direct coupling to peptides and proteins. Typical examples of suitable supports are the resin activated-CH SEPHAROSE™ 4B from Pharmacia (Sweden), the resin PROTEIN-PAK™ (Waters, USA) the resin EUPERGIT™ C30 N (Rohm & Haas, Germany), or AFFI-GEL™ from BioRad (USA).

Step (i) is preferably carried out in the presence of a weakly basic buffer solution having a pH value of from 8.5 to 9.0.

Step (iii) is preferably performed with a neutral buffer such as, for example, a 25 mM Bis-Tris solution having pH 6.5, or a 50 mM phosphate buffer solution having pH 7.0.

Step (v) is preferably carried out by using a neutral buffer having a low ionic strength such as, for example, a 25 mM Bis-Tris solution having pH 6.5.

Examples of dissociating eluents useful in step (vi) comprise acid or basic aqueous solutions. Typical examples comprise aqueous solutions of acetic acid at pH 2.5 or of sodium bicarbonate at pH 9.0.

This separation and purification technique is widely described in the literature [Narayanan, S. R., "Preparative affinity chromatography of proteins" J. Chromatogr., 658:237–258 (1994), as well as references quoted therein; Lowe, C. R., "Laboratory technique in Biochemistry and Molecular Biology", Work and Burdon, vol. 7, part 2, Elsevier, N. Holland, Amsterdam; Ey et al. Immunochemistry, 15:429 (1978)].

The compounds of this invention may also be used in the qualitative or quantitative determination of immunoglobulins according to the well known ELISA technique.

A typical example of a method for quantitative determination of an immunoglobulin or a mixture of immunoglobulins according to the ELISA technique comprises:

(1) immobilizing a compound capable of binding itself non covalently to at least one immunoglobulin on a microtiter plate for ELISA determination, (2) incubating a sample containing the immunoglobulin or the immunoglobulins to be determined on said microtiter plate, (3) washing said microtiter plate, (4) detecting the thus formed immobilized complex compound/immunoglobulin, and is characterized in that the compound capable of binding itself non covalently to at least one immunoglobulin is a compound of formula (I) where $X_1$, $X_2$, n and R have the above mentioned meanings.

The analytical determination of immunoglobulins according to the ELISA technique is widely described in the literature ("Immunochemistry in practice", Johnstone & Thorpe, (1987), Blackwell, Oxford, UK).

Preferably, step 1 is carried out using a plastic microtiter plate such as, for example, of PVC, with 96 well filled with 0.1M sodium bicarbonate solutions having pH 9.0 and containing variable amounts of a ligand (0–50 μg/well). After 24 h incubation, excess solution is removed, and the microtiter plates are washed with phosphate buffer and the wells are filled with a 3% bovine albumin solution to eliminate a specific interaction sites.

In step 2, microtiter plates are washed with phosphate buffer and the wells are filled with solutions containing an immunoglobulin, preferably derivatized with biotin. Microtiter plates are then incubated for 4–18 h at 20°–37° C.

Washing in step 3 is preferably carried out with phosphate buffer.

Step 4 is performed by adding to each well a solution of avidin conjugated to peroxidase. After 2 h incubation, microtiter plates are washed, preferably again with a phosphate buffer. Then a solution of o-phenylenediamine is added and color formation is detected with a suitable ELISA reader.

These and further features of the present invention will result more clearly from the following examples and the enclosed figures.

BRIEF DESCRIPTION OF THE DRAWINGS

FIG. 2 shows the electrophoretic analysis on polyacrylamide gels of the fractions deriving from the purification of rabbit immunoglobulins by using the compound of formula (H-L-Arg-L-Thr-L-Tyr-)$_4$-Lys$_2$-Lys-Gly-OH, with different buffers and different amounts of sera.

Figure 1:
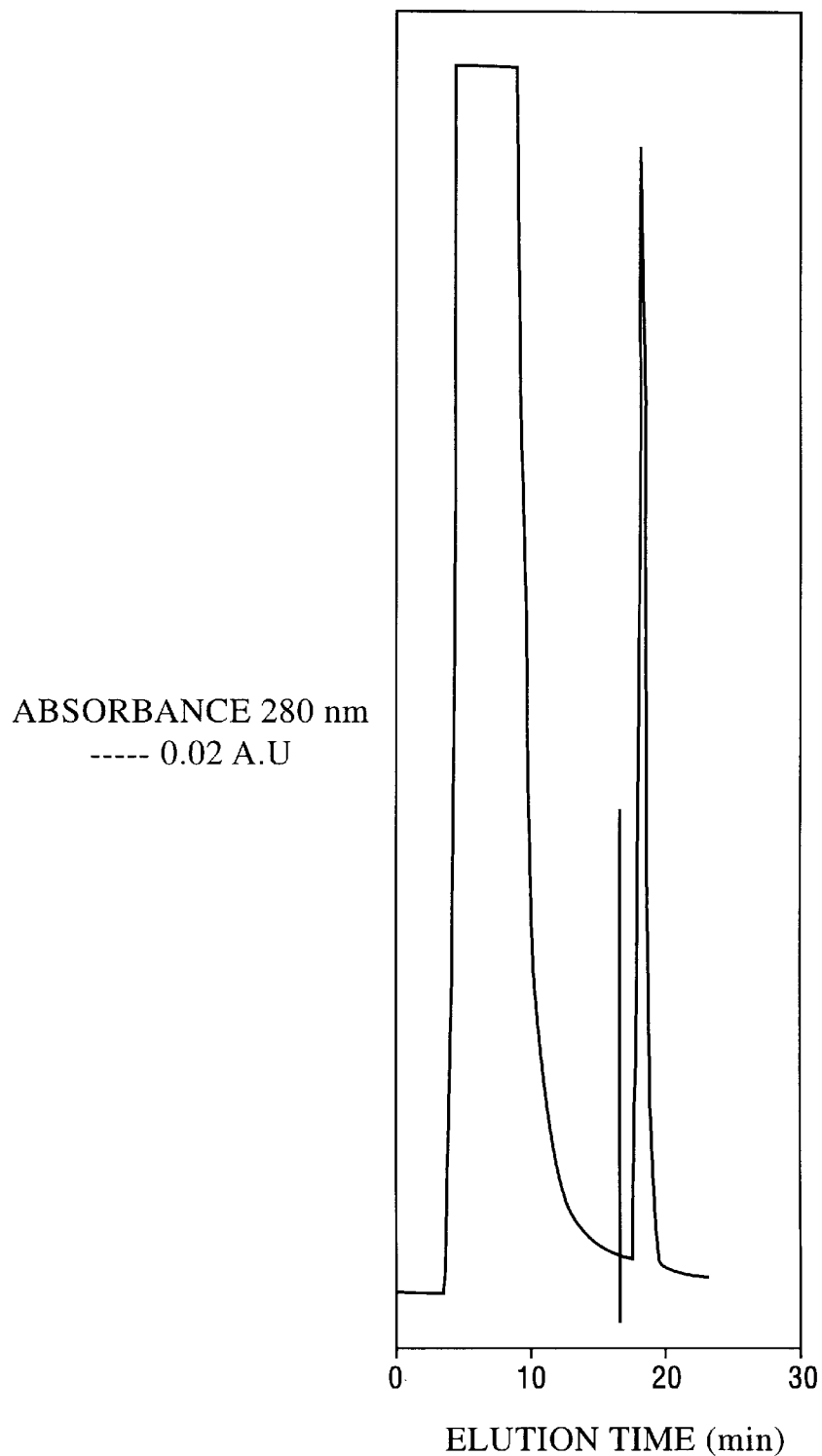
FIG. 1 shows the purification of rabbit immunoglobulin from crude serum using affinity chromatography on a column prepared by immobilization of the compound of formula (H-L-Arg-L-Thr-L-Tyr-)$_4$-Lys$_2$-Lys-Gly-OH.

For the solid phase synthesis of compounds of formula (I) it has been used an automatic peptide synthesizer from Applied Biosystems (Foster City, Calif., USA)—model 431A, software version 1.1—following the synthesis procedure recommeded by the manufacturer and based on methodology known and widely reported in the literature (Atherton and Sheppard, 1988, Solid phase peptide synthesis: A practical approach, IRL Press, Oxford).

In the following examples "Cat. No." means catalogue number.

The following examples are given to better illustrate this invention without limiting it in any way.

EXAMPLE 1

Solution preparation of a peptide of formula (I) (X$_1$=Arg, X$_2$=Tyr, n=1, R=OH) where the amino acids have D configuration The synthesis started from the preparation of the protected dipeptide Z-D-Thr(tBu)-D-Tyr(tBu)-OMe to which subsequently was coupled, first removing the Z protecting group at the N-terminus, the protected arginine amino acid to obtain the derivative Boc-D-Arg(Pbf)-D-Thr(tBu)-D-Tyr (tBu)-OMe, which after complete deprotection led to peptide of formula (I).

a) Preparation of H-D-Tyr(tBu)-Ome (M.W. 251 amu)

To a suspension of H-D-Tyr(tBu)-OH (3.55 g, 15 mmoles, Bachem Feinchemikalien, cat. No F-2170) in CH$_3$OH (100 ml), chilled to −15° C., there were added 3.54 g of SOCl$_2$ (30 mmoles, Aldrich, cat. No 23,046-4). After shaking 2 h at room temperature and 2 h at 90° C., the solvent was removed by evaporation and the residue dried over KOH for one night. There were thus obtained 4.21 g of crude product as hydrochloride salt (14.7 mmoles). Yield 98%.

b) Preparation of Z-D-Thr(tBu)-D-Tyr(tBu)-OMe (M.W. 541 amu)

To a solution of 7.21 g (10 mmoli) of Z-D-Thr(tBu)-OH (DCHA (Bachem Feinchemikalien, cat. No C-1480) and 1.65 ml (16.2 mmoles) of N-methyl morpholine (NMM, Sigma, cat. No M-7889) in 75 ml of dry N-methyl pyrrolidone (NMP), there were added drop-wise at −10° C., under shaking, 2.12 ml (16.2 mmoles) of isobutylchloroformate (IBCF, Sigma, cat. No 1-3253) diluted in 9 ml of CHCl$_3$. After 20 minutes, there was added drop-wise a solution of 4.21 g (14.7 mmoles) of H-D-Tyr(tBu)-OMe·HCl and 1.75 ml of NMM, in 75 ml of NMP. Then NMM (about 3 ml) was further added to reach a pH of from 7.5 to 8.0.

The reaction mixture was kept under shaking for 2 h at 0° C. and then overnight at room temperature.

The precipitated salts were filtered and the solution was concentrated by flash chromatography on silica gel using a mixture of AcOEt-hexane as eluent. The desired product (4.03 g; 7.45 mmoles), was obtained in the form of pure oil (TLC).

c) Preparation of H-D-Thr(tBu)-D-Tyr(tBu)-OMe (M.W. 407 amu)

4.03 g of Z-D-Thr(tBu)-D-Tyr(tBu)-OMe (7.45 mmoles) were dissolved in 250 ml of CH30H. After addition of 850 mg of 10% Pd on activated charcoal (Fluka, cat. No 75990) a hydrogen stream was blown on the solution at room temperature under shaking for 4 h. The hydrogenation reaction was monitored by TLC. After removal of the catalyst by filtration and evaporation of the filtrate, 2.88 g (7.08 mmoles, yield 95%) of H-D-Thr(tBu)-D-Tyr(tBu)-OMe were obtained in the form of pure oil (TLC).

d) Preparation of Boc-D-Arg(Pbf)-D-Thr(tBu)-D-Tyr (tBu)-OMe (M.W. 916 amu)

A clear solution of 3.73 g (7.08 mmoles) of Boc-D-Arg (Pbf)-OH (Bachem Feinchemikalien, cat. No A-3750) in 75 ml of dry NMP, comprising 0.85 ml (7.79 mmoles) of NMM was chilled to −10° C. under shaking. Then, 1.02 ml (7.79 mmoles) of IBCF diluted in 6 ml of CHCl$_3$ were added drop-wise. After 30 minutes, a solution of 2.88 g (7.08 mmoles) of H-L-Thr(tBu)-L-Tyr(tBu)-OMe in 75 ml of CHCl$_3$ was added drop-wise in 20 minutes. The reaction mixture was kept for 2 h at 0° C. and overnight at room temperature. The solvent was evaporated under vacuum and the crude material was purified by flash chromatography on silica gel column, using a mixture of AcOEt-hexane as eluent. There were thus obtained 5.58 g (6.08 mmoles, yield 86%) of Boc-D-Arg(Pbf)-D-Thr(tBu)-D-Tyr(tBu)-OMe, as pure oil (TLC and RP-HPLC).

e) Preparation of H-D-Arg-D-Thr-D-Tyr-OH (M.W. 438 amu)

The oil was treated for 2 h with 100 ml of a mixture having the following composition

TABLE 1

| Component | % (v/v) |
| --- | --- |
| Trifluoroacetic acid (TFA, Sigma Chem. Co., St. Louis, Mo) | 83 |
| H$_2$O | 4 |
| Phenol (Sigma) | 6 |
| Thioanisol (Sigma) | 5 |
| Triisopropylsilane (TIS, Sigma) | 2 |

The solution was concentrated to about 10 ml by vacuum evaporation of the trifluoroacetic acid, and the crude peptidic material was precipitated by addition of 150 ml of cold ethyl ether. After removal of the precipitating agent, a subsequent washing with 100 ml of cold ethyl ether was carried out to better solubilize the scavengers. All the peptidic material, was dissolved in 50 ml of H$_2$O/CH$_3$CN/TFA 50/50/0.1 and then frozen and lyophilized.

1.89 g of the tripeptide H-D-Arg-D-Thr-D-Tyr-OH, equivalent to 4.32 mmoles, were thus recovered. Yield, 71%. RP-HPLC analysis of a 5 µg aliquot the product showed that it was 97% pure.

Working in a similar way the following additional compounds have been prepared:

H-L-Arg-L-Thr-L-Tyr-OH

H-L-Tyr-L-Thr-L-Arg-OH

H-D-Tyr-D-Thr-D-Arg-OH

Preparation yields, final purity and experimentally observed molecular weigth as determined by mass spectrometry are shown in the following Table A.

TABLE A

| Compound | Yield (%) | Purity (%) | Observed M.W. | Theoretical M.W. |
|---|---|---|---|---|
| H—D—Arg—D—Thr—D—Tyr—OH | 71 | 97 | 438.3 | 438 |
| H—L—Arg—L—Thr—L—Tyr—OH | 79 | 97 | 438.7 | 438 |
| H—L—Tyr—L—Thr—L—Arg—OH | 76 | 96 | 438.1 | 438 |
| H—D—Tyr—D—Thr—D—Arg—OH | 77 | 97 | 438.5 | 438 |

EXAMPLE 2

Solid phase preparation of a peptide of formula (I) ($X_1$=Arg, $X_2$=Tyr, n=4, R=Lys-Lys($\epsilon$Lys)-Gly) where the amino acids have L configuration.

The peptide preparation was carried out in the solid phase using an automatic peptide synthesizer from APPLIED BIOSYSTEMS Mod 431 A following the Fmoc/HOBt/DCC methodology (Konig, W., and Geiger, R., 1970, Chem. Ber. 103, 788–798.) and following protocols as recommeded by the manufacturer (APPLIED BIOSYSTEM, USA).

The preparation was carried out a 0.1 mmole scale starting from a acid-labile resin for peptide synthesis prederivatized with glycine (chlorotritylichloridric NOVOBIOCHEM Cat No. 04-12-2800, 0.1 mmole) protected at the N-terminal amino group with the Fmoc group, which, in the first synthesis cycle, was deprotected by treatment with 3.0 ml of piperidine ( 20 % in N-methyl-2-pyrrolidone (ABI Cat No. 400629) for 14 minutes, at room temperature under stirring.

The deprotected resin was then washed 5 times with 2.5 ml of N-methyl-2-pyrrolidone (Merck Cat. No. 806072) for 9 minutes under shaking at room temperature.

Then the amino acid Fmoc-Lys(Fmoc) (Novabiochem Cat. No. 04-12-1085) acid was attached, previously transformed into the corresponding benzotriazole compound active ester by incubation with a solution of hydroxybenzotriazole (HOBt, APPLIED BIOSYSTEMS, Cat. No 400662) and dicyclohexylcarbodiimide (DCC, APPLIED BIOSYSTEMS, Cat. No 400663). After removal of the Fmoc protecting groups in $\alpha$ and $\epsilon$ position, a second coupling of Fmoc-Lys(Fmoc) (NOVABIOCHEM Cat. No. 04-12-1085) was accomplished, to form the central tetrameric core R. Then Fmoc-Tyr(tBu)-OH (BACHEM FEINCHEMIKALIEN Cat. No B-1255) acid was attached, previously transformed into the corresponding benzotriazole compound active ester by incubation with a solution of hydroxybenzotriazole (HOBt, APPLIED BIOSYSTEMS, Cat No 400662) and dicyclohexylcarbodiimide (DCC, APPLIED BIOSYSTEMS, Cat No 400663).

The suspension resin/activated amino acid was shaken for 51 minutes. During the coupling of the tyrosine residue the activation of the threonine residue was accomplished. 1 mmole of Fmoc-Thr(tBu)-OH (BACHEM FEINCHEMI-KALIEN Cat No B-1245) was transformed in the corresponding benzotriazole compound active ester by incubation with a solution of hydroxybenzotriazole (HOBt, APPLIED BIOSYSTEMS, Cat No 400662) and dicyclohexylcarbodiimide (DCC, APPLIED BIOSYSTEMS, Cat No 400663).

When the coupling of tyrosine was over, the resin was extensively washed with N-methyl-pirrolidone (NMP). Removal of Fmoc group was accomplished by treatment with 3 ml of 20% piperidine in NMP. After several washes with NMP, the amino acid threonine previously activated, was transferred on the resin. The coupling reaction lasted for 51 minutes, and during that time the third amino acid arginine was activated. The derivative Fmoc-Arg(Pbf)-OH (BACHEM FEINCHEMIKALIEN Cat No B-2375) was used. The activation method was the same as described in relation to threonine activation.

After threonine acylation and subsequent removal of the Fmoc group with piperidine, activated arginine was transferred on the resin for the coupling step. After the required washings for removing the amino acid excess and the deprotection of the Fmoc groups even on the arginine residue, the resin was washed extensively first with NMP and then with cichloromethane (DCM). At the end, the resin was dried by an argon stream. 215.8 mg of resin were recovered.

A fully protected tetramer of formula

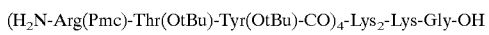

has been prepared by treating the resin with a mixture of acetic acid (Merck Cat. No. 63), dichloro methane (Merck Cat. No. 6050), and ethanol (Merck Cat. No. 8006) in the ratio 80:10:10 v/v.

This treatment allows the detachment of the peptide from the resin but not of the amino acid side chain protecting groups.

Alternatively, a fully deprotected tetramer of formula

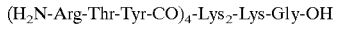

has been obtained by treating the resin with 10 ml of a mixture of trifluoroacetic acid and scavengers having the composition shown in Table 1, Example 1.

The solution, was concentrated to about 1 ml by evaporation of the trifluoroacetic acid under vacuum. The crude peptidic material was precipitated by adding 30 ml of cold ethyl ether. After removal of the precipitation agent, a second washing with 30 ml of cold ethyl ether was carried out to further solubilize the scavengers. All the peptidic material, dissolved in 5 ml of $H_2O/CH_3CN/TFA$ 50/50/0.1, was frozen and lyophilized.

103.8 mg of the tetrameric tripeptide (H-L-Arg-L-Thr-L-Tyr-)$_4$-Lys$_2$-Lys-COOH were recovered. RP-HPLC analysis of a 5 $\mu$g aliquot of the product showed a purity close to 97%.

Working in a similar way there were prepared the additional compounds shown in the Table B.

TABLE B

| Compound | Yield (%) | Purity (%) | Observed M.W. | Theoretical M.W. |
|---|---|---|---|---|
| (H—D—Arg—D—Thr—D—Tyr—)$_4$—Lys$_2$—Lys—GlyOH | 75 | 97 | 438.3 | 2142 |
| (H—L—Arg—L—Thr—L—Tyr—)$_4$—Lys$_2$—Lys—Gly—OH | 82 | 97 | 438.7 | 2142 |
| (H—L—Tyr—L—Thr—L—Arg—)$_4$—Lys$_2$—Lys—Gly—OH | 79 | 96 | 438.1 | 2142 |
| (H—D—Tyr—D—Thr—D—Arg—)$_4$—Lys$_2$—Lys—Gly—OH | 81 | 97 | 438.5 | 2142 |

EXAMPLE 3

Immobilization of peptides of Examples 1 and 2 on Activated CH-Sepharose 4B and purification of immunoglobulins from sera by affinity chromatography.

The peptide of formula (H-L-Arg-L-Thr-L-Tyr-)$_4$-Lys$_2$-Lys-Gly-OH (5 mg) was dissolved in 5 ml of 0.1M sodium bicarbonate buffer pH 9.0 and then added to 1.2 g of activated resin CH-Sepharose 4B (Pharmacia, Uppsala, Sweden Cat. No. 17-0490-01), which is a chromatographic support for affinity chromatography preactivated for the direct coupling to peptides and proteins. The suspension was shaken for 24 h and the coupling level was monitored by taking aliquots of the reaction mixture at different times and subsequent RP-HPLC analysis.

Approximately 90% of initial peptide resulted covalently linked to the resin after 24 h. The derivatized resin was washed with 50 ml of 1M TRIS pH 9.0 and then packed on a glass column (100×6.6 mm I.D.).

Working in a similar way with other compounds of this invention, there were obtained the immobilization yields shown in Table C.

TABLE C

| Compound | Immobilization Yield (%) |
|---|---|
| (H—D—Arg—D—Thr—D—Tyr—)$_4$—Lys$_2$—Lys—GlyOH | 89 |
| (H—L—Arg—L—Thr—L—Tyr—)$_4$—Lys$_2$—Lys—Gly—OH | 90 |
| (H—L—Tyr—L—Thr—L—Arg—)$_4$—Lys$_2$—Lys—Gly—OH | 85 |
| (H—D—Tyr—D—Thr—D—Arg—)$_4$—Lys$_2$—Lys—Gly—OH | 89 |
| H—D—Arg—D—Thr—D—Tyr—OH | 95 |
| H—L—Arg—L—Thr—L—Tyr—OH | 93 |
| H—L—Tyr—L—Thr—L—Arg—OH | 96 |
| H—D—Tyr—D—Thr—D—Arg—OH | 94 |

In order to purify immunoglobulins, the column was equilibrated with a 25 mM BIS-TRIS buffer (SIGMA, Cat. B9754) pH 6.5, at a flow rate of 1 ml/min, while the eluent was monitored at 280 nm. One milliliter of crude rabbit serum (SIGMA Cat. No. R 9133) was then loaded on the column, and after elution of non retained material at the column void volume, the eluent was changed to 0.1M acetic acid.

Material desorbed by such a treatment was collected and analyzed by electrophoretic analysis on a polyacrylamide gel.

The purification of rabbit immunoglobulins from crude serum by affinity chromatography is shown in FIG. 1 while the electrophoretic analysis of the collected fractions is shown in FIG. 2. As clearly shown by the electrophoretic analysis, the column was able to retain the immunoglobulin fraction from the crude serum, while albumin was not retained and was eluted at the column void volume. Furthermore, in FIG. 2 are also shown the electrophoretic analyses corresponding to several rabbit immunoglobulins purifications obtained after equilibration of the affinity column with different buffers, namely 0.1M ammonium acetate pH 5.7 (A), 0.1M sodium phosphate pH 7.0 (B), or 0.1M sodium phosphate pH 8.5 (C). As clearly shown by the electrophoretic analysis of the fractions desorbed by treatment with acetic acid 0.1M, in all the three cases an optimal purification of immunoglobulins from contaminants was achieved.

Furthermore, the column showed a remarkable purification capability, allowing purification of immunoglobulins from 0.5 ml (E), 1 ml (F), and 1.5 ml (G) of serum. The column selectivity resulted to be superior to that of columns with immobilized protein A. Indeed, purification of the same serum on columns of immobilized protein A having the same dimensions provided purified fractions always comprising traces of albumin. The purification capability of both monomeric and multimeric peptides under examination and analogs thereof prepared with aminoacids in configuration L or D resulted to be similar and did not depend on the type of affinity chromatography support which was used. Indeed similar results were attained with other supports such as Protein-Pak (Waters, USA), Eupergit C30N (Sigma, USA) and Affi-Gel (Bio-Rad, USA).

Similar results were obtained with columns prepared with immobilized peptides of formula (1) in the isolation of IgG from mouse, rat, goat, sheep, horse, human, and bovine sera, as well as of chicken IgY, human IgA, and human IgM, from crude sources.

SEQUENCE LISTING

< 1 6 0 > 4

< 2 1 0 > 1
< 2 1 1 > 4
< 2 1 2 > PRT
< 2 1 3 > Artificial Sequence

< 2 2 0 >
< 2 2 3 > Description of Artificial Sequence:Synthetic

<400>1

Gly Gly Gly Gly
 1

<210>2
<211>5
<212>PRT
<213>Artificial Sequence

<220>
<223>Description of Artificial Sequence:Synthetic

<400>2

Gly Gly Gly Gly Gly
 1               5

<210>3
<211>5
<212>PRT
<213>Artificial Sequence

<220>
<223>Description of Artificial Sequence:Synthetic

<400>3

Gly Ala Gly Ala Gly
 1               5

<210>4
<211>7
<212>PRT
<213>Artificial Sequence

<220>
<223>Description of Artificial Sequence:Synthetic

<400>4

Ala Gly Ala Gly Ala Gly Ala
 1               5

We claim:

1. A compound of formula $$(H_2N-X_1-Thr-X_2-CO)_4-Lys_2-Lys-Gly-OH \quad (1A)$$

where $X_1$ and $X_2$, different from one another, are amino acid residue arginine or tyrosine in configuration L or D, wherein the hydroxy group of threonine and tyrosine and the guanidine moiety of arginine are optionally protected by a protecting group conventionally used in peptide chemistry for protecting the hydroxy group and the guanidine moiety, respectively.

* * * * *